United States Patent
Seto et al.

(10) Patent No.: US 7,435,215 B2
(45) Date of Patent: Oct. 14, 2008

(54) ENDOSCOPE

(75) Inventors: Hideyuki Seto, Hino (JP); Shigeyasu Kishioka, Kokubunji (JP); Toshiyuki Kubonoya, Akiruno (JP)

(73) Assignee: Olympus Corporation, Tokyo (JP)

( * ) Notice: Subject to any disclaimer, the term of this patent is extended or adjusted under 35 U.S.C. 154(b) by 11 days.

(21) Appl. No.: 10/764,862

(22) Filed: Jan. 26, 2004

(65) Prior Publication Data
US 2004/0158159 A1 Aug. 12, 2004

(30) Foreign Application Priority Data
Jan. 28, 2003 (JP) .............................. 2003-019248
Jan. 28, 2003 (JP) .............................. 2003-019249

(51) Int. Cl.
*A61B 1/00* (2006.01)
(52) U.S. Cl. ........................ 600/133; 600/106; 600/179; 600/109; 600/160; 600/110
(58) Field of Classification Search ................. 600/109, 600/112, 131, 160, 178, 478; 606/15; 607/88
See application file for complete search history.

(56) References Cited

U.S. PATENT DOCUMENTS

| | | | | |
|---|---|---|---|---|
| 5,060,632 A | * | 10/1991 | Hibino et al. ................ | 600/109 |
| 5,372,124 A | * | 12/1994 | Takayama et al. ........... | 600/106 |
| 5,392,067 A | * | 2/1995 | Konno et al. ................. | 348/72 |
| 5,408,996 A | * | 4/1995 | Salb ............................ | 600/317 |
| 5,409,483 A | * | 4/1995 | Campbell et al. ............ | 606/15 |
| 5,772,580 A | * | 6/1998 | Utsui et al. .................. | 600/160 |
| 6,080,101 A | * | 6/2000 | Tatsuno et al. .............. | 600/112 |
| 6,315,712 B1 | * | 11/2001 | Rovegno ..................... | 600/109 |
| 6,432,046 B1 | * | 8/2002 | Yarush et al. ................ | 600/179 |
| 6,547,721 B1 | * | 4/2003 | Higuma et al. .............. | 600/133 |
| 6,970,308 B2 | * | 11/2005 | Otsuka ........................ | 359/819 |

FOREIGN PATENT DOCUMENTS

| | | |
|---|---|---|
| JP | 11-23983 | 1/1999 |
| JP | 11-151200 | 6/1999 |
| JP | 2003-190080 | 7/2003 |

* cited by examiner

*Primary Examiner*—Brian L. Casler
*Assistant Examiner*—Sanjay Cattungal
(74) *Attorney, Agent, or Firm*—Scully, Scott, Murphy & Presser, P.C.

(57) ABSTRACT

An inserting portion has, at the proximal end thereof, an operating portion having a bending lever for bending operation. The operating portion has, on the front end side thereof, a grip portion gripped by an operator. The grip portion has therein a plate frame as an internal structure for ensuring predetermined strength. At the notch portion formed by partly notching the frame, an image pick-up unit is mounted to form an optical image transmitted by image guiding fibers to a CCD via a relay optical system. The image pick-up unit is fixed to the frame via an attaching member. Thus, predetermined strength is assured and the image pick-up unit is compactly accommodated with simple structure. A predetermined image pick-up function using the image pick-up unit is held without the action of high tension to the image guiding fibers by mounting a bending portion to the image guiding fibers.

9 Claims, 6 Drawing Sheets

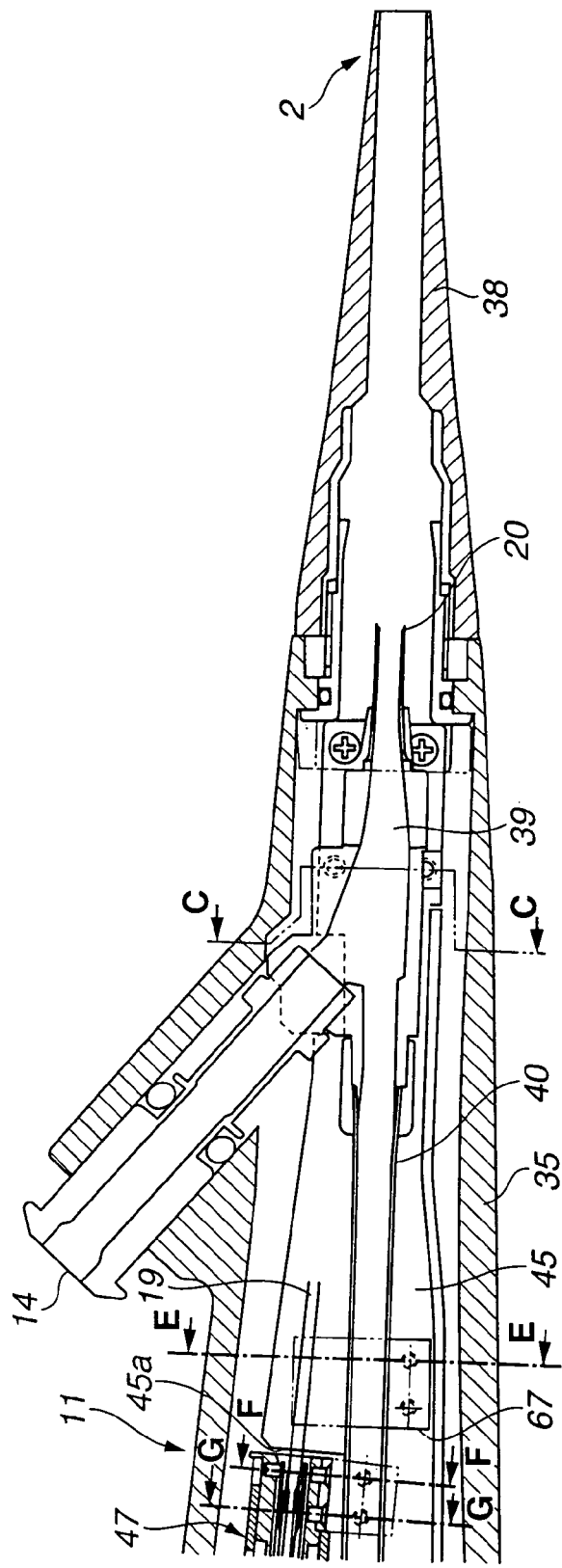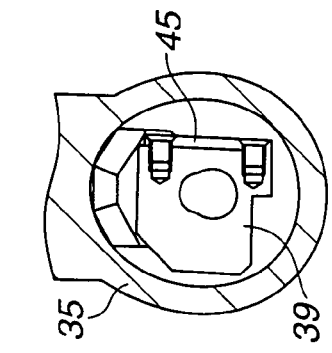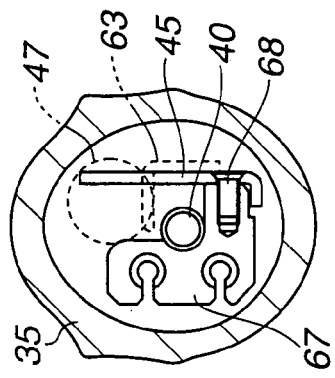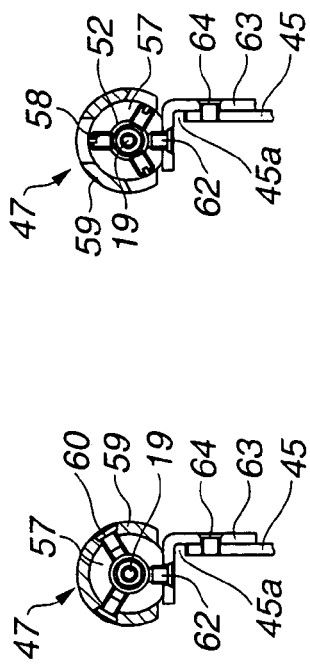
FIG. 4A  FIG. 4B  FIG. 4C  FIG. 4D  FIG. 4E

ENDOSCOPE

This application claims benefit of Japanese Application Nos. 2003-19248 filed in Japan on Jan. 28, 2003 and 2003-19249 filed in Japan on Jan. 28, 2003, the contents of which are incorporated by this reference.

BACKGROUND OF THE INVENTION

1. Field of the Invention

The present invention relates to an endoscope including an inserting portion with a thin diameter and an operating portion having therein an electric device such as an image pick-up unit.

2. Description of the Related Art

In recent years, an endoscope has widely been used in medical and industrial fields. Further, an endoscope is commonly used, having therein an image pick-up unit incorporating an image pick-up device which simply records an endoscope image obtained by the endoscope and easily edits and reuses it.

A micro-sized image pick-up device is developed. In the case of an endoscope having an inserting portion with a thin diameter for the bronchi, the image pick-up device is mounted at the distal end portion of the inserting portion and then the outer diameter of the inserting portion is larger.

Therefore, an endoscope having an image pick-up device in an operating portion is disclosed. For example, Japanese Unexamined Patent Application Publication No. 11-23983 (hereinafter, referred to as a document 1) discloses the above-mentioned endoscope as a well-known art.

According to the well-known art disclosed in the document 1, the operating portion has the image pick-up device near at the proximal end thereof, and an optical fiber is inserted in the inserting portion so as to transmit an optical image to the proximal end of the optical fiber at which the image pick-up device is mounted. The optical image of a subject is formed onto the image pick-up device via an image pick-up optical system mounted facing the proximal end of the optical fiber. According to the document 1, the proximal end of the optical fiber and an image pick-up unit (TV camera) are incorporated in the operating portion on the back side of a portion branched to a universal cord.

Further, a well-known art disclosed in Japanese Unexamined Patent Application Publication No. 11-151200 (hereinafter, referred to as a document 2) discloses an endoscope in which an optical image of a subject is formed onto an image pick-up surface of an image pick-up device in a grip portion having the proximal end of an optical fiber for transmitting an image, which is inserted in an inserting portion to be inserted into the eyeball.

According to the document 2, the optical fiber inserted in the inserting portion is mounted so that it is extended substantially straight in the grip portion, and the optical image of the subject is formed onto the image pick-up device via a projecting lens facing the optical fiber.

In the case of a so-called soft endoscope having a soft inserting portion and a hard endoscope having a hard inserting portion, the endoscope having a mechanism for bending the distal end portion of the inserting portion includes an optical fiber for transmitting the image which is generally designed with flexure in consideration of the following points.

Upon bending the inserting portion or distal end portion of the optical fiber, the excessive stretch and the resultant damage of the optical fiber is prevented.

The variation in length of the optical fiber or the inserting portion is absorbed.

A channel tube for absorbing and supplying air and solution, or a wire for bending is avoided.

The optical fiber upon assembly is easily attached.

SUMMARY OF THE INVENTION

According to the present invention, an endoscope comprises: an elongated inserting portion; and an operating portion which is mounted at the proximal end of the inserting portion and includes a grip portion gripped by an operator, wherein the operating portion has therein a plate frame and the plate frame has a notch portion to mount an image pick-up unit.

Further, according to the present invention, an endoscope comprises: a long inserting portion; and an operating portion which is mounted on the proximal end side of the inserting portion and which has a grip portion capable of being gripped by an operator. The endoscope further comprises: an electric device forming the endoscope; an internal structure mounted in the operating portion, which is inserted in the grip portion from the proximal end side thereof to the distal end side; a notch portion mounted to the internal structure; and electric device mounting means which is mounted to the internal structure and mounts the electric device to the notch portion.

In addition, an endoscope comprises: a long inserting portion; a grip portion which is mounted on the proximal end side of the inserting portion and which can be gripped by an operator; an objective optical system which is mounted to a distal end portion of the inserting portion and which can transmit an optical image of a subject into the inserting portion; image guiding fibers which can transmit the optical image incident from the distal end side via the objective optical system and which is inserted to the inserting portion so that the proximal end side extends in the grip portion from the inserting portion; an optical system output portion which is mounted on the proximal end side of the image guiding fibers and which outputs the optical image transmitted from the distal end side; and an image pick-up unit which is optically connected to the optical image output portion and which can pick up the optical image transmitted from the optical image output portion, wherein the optical axis of the optical image outputted to the image pick-up unit from the optical image output portion is deviated from the central axis of a portion at which the image guiding fibers are extended in the grip portion.

The above and other objects, features and advantages of the invention will become more clearly understood from the following description referring to the accompanying drawings.

BRIEF DESCRIPTION OF THE DRAWINGS

FIG. 4A is a diagram showing one example of the internal configuration of a grip portion in the operating portion;

FIG. 4B is a diagram showing another example of the internal configuration of the grip portion in the operating portion;

FIG. 4C is a diagram showing another example of the internal configuration of the grip portion in the operating portion;

FIG. 4D is a diagram showing another example of the internal configuration of the grip portion in the operating portion;

FIG. 4E is a diagram showing another example of the internal configuration of the grip portion in the operating portion;

DETAILED DESCRIPTION OF THE PREFERRED EMBODIMENTS

Hereinbelow, a description is given of embodiments of the present invention.

First Embodiment

Figure 1:
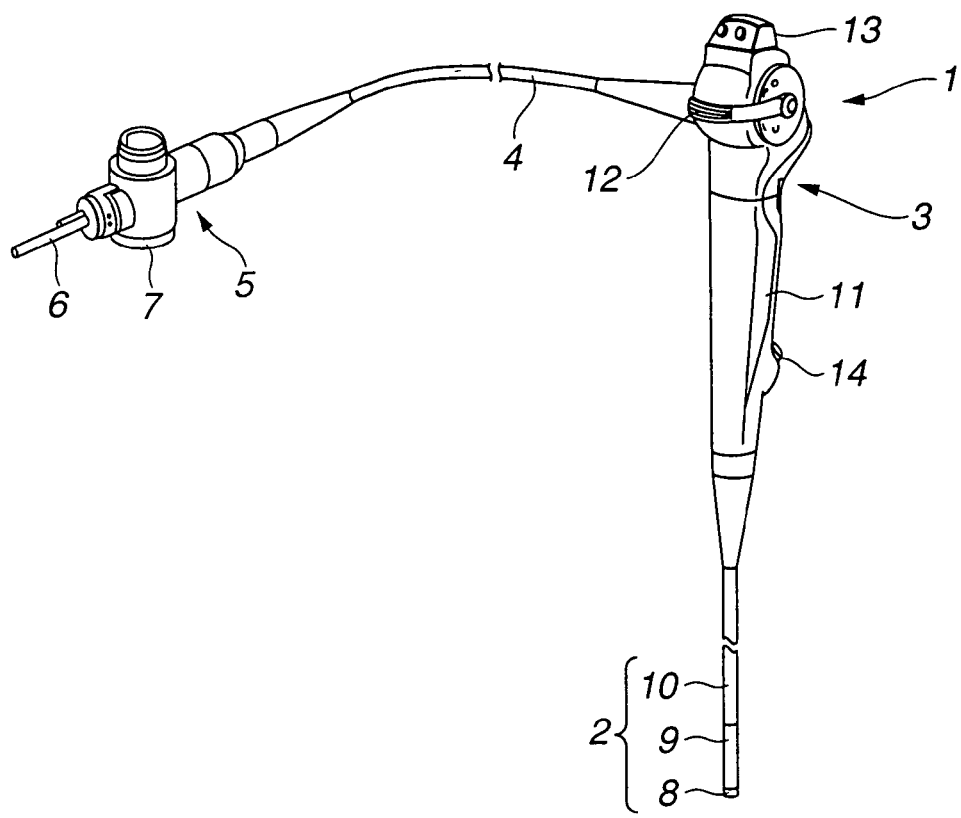
FIG. 1 is a perspective view showing the appearance of an endoscope according to a first embodiment of the present invention.
Figure 2:
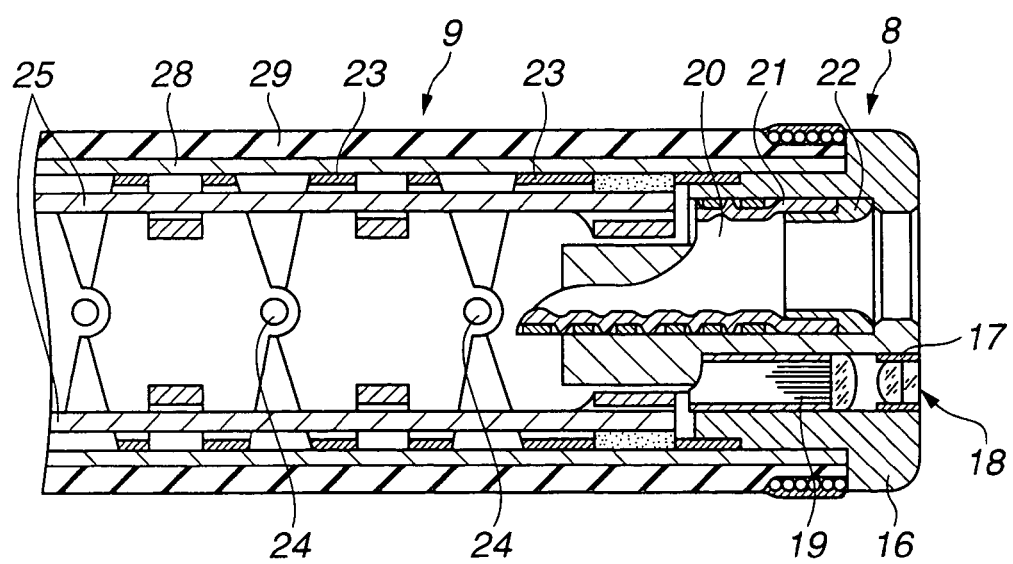
FIG. 2 is a cross-sectional view showing the internal configuration of an inserting portion on the distal end side thereof.
Figures 3A, 3B:
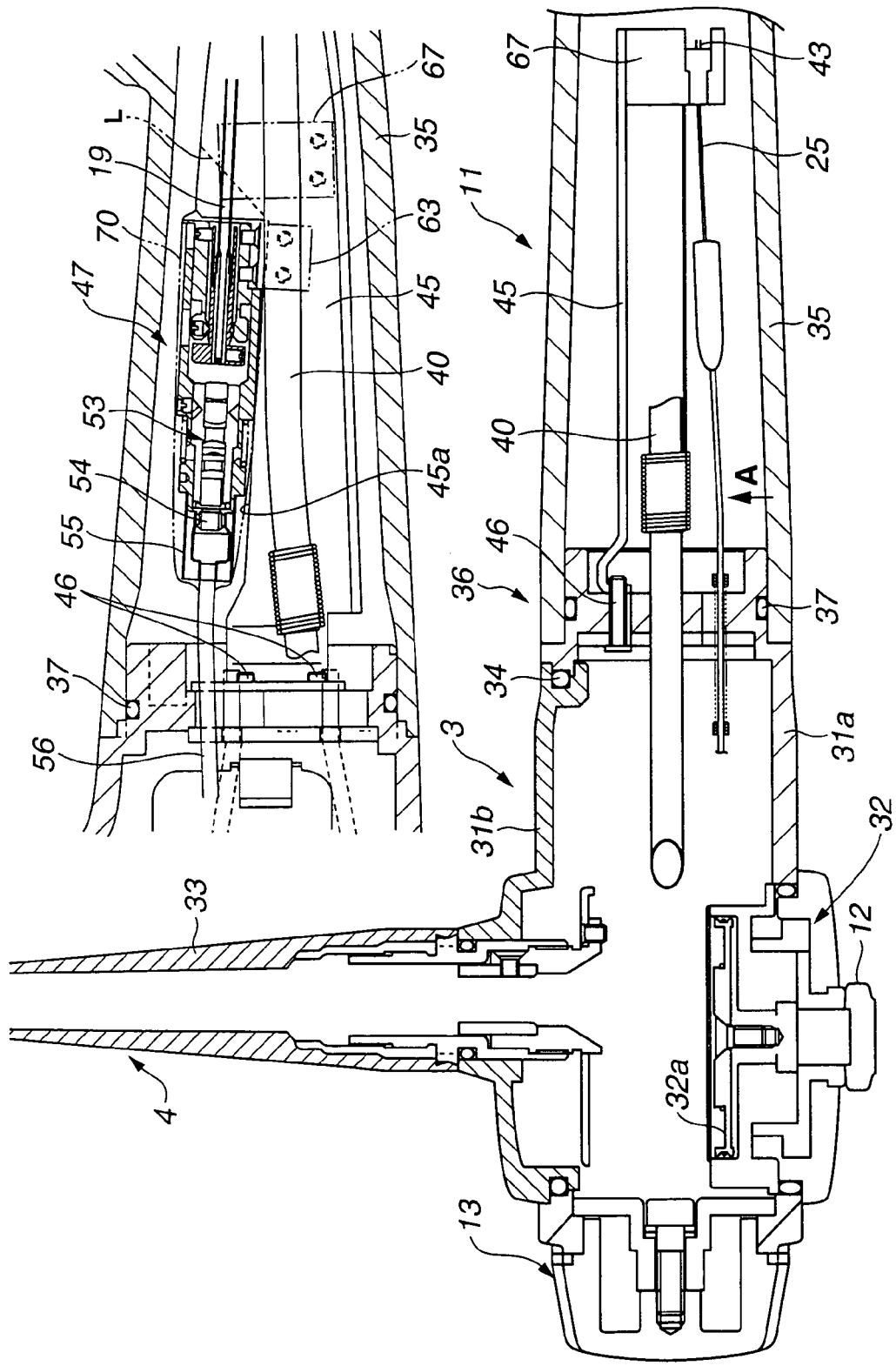
FIG. 3A is a cross-sectional view showing one example of the internal configuration and the like of an operating portion.
FIG. 3B is a cross-sectional view showing another example of the internal configuration of the operating portion.
Figure 5:
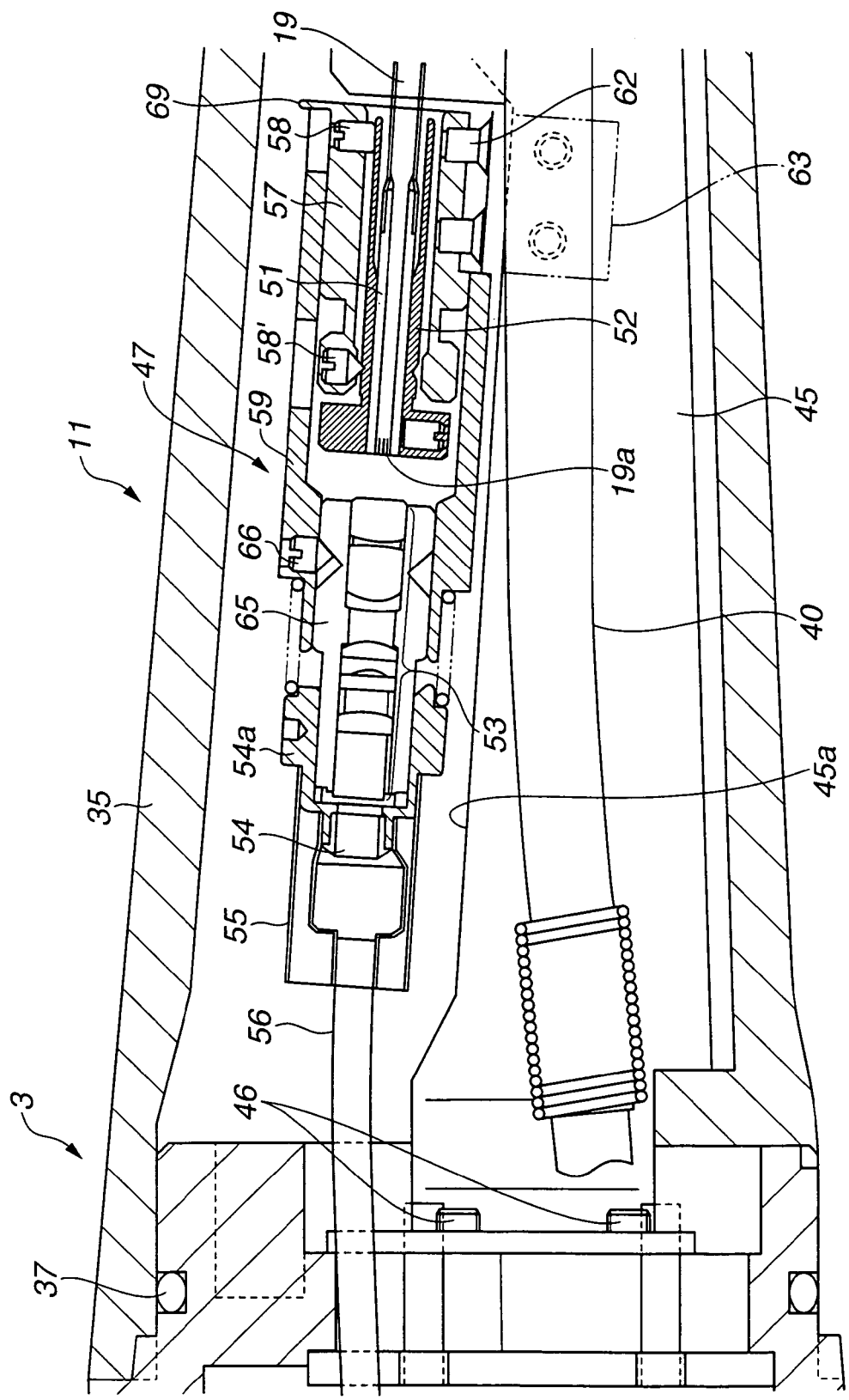
FIG. 5 is an enlarged cross-sectional view showing the configuration of an image pick-up unit.

FIGS. 1 to 5 relate to the first embodiment of the present invention, FIG. 1 shows the appearance of an endoscope according to the first embodiment, FIG. 2 shows the internal configuration of an inserting portion on the distal end side thereof, FIGS. 3A and 3B show examples of the internal configuration and the like of an operating portion, FIGS. 4A and 4B show examples of the internal configuration of a grip portion in the operating portion, and FIG. 5 shows the configuration of an image pick-up unit.

Referring to FIG. 1, an endoscope 1 according to the first embodiment of the present invention comprises an elongated inserting portion 2 with flexure, which is inserted in the body cavity, an operating portion 3 mounted at the proximal end of the inserting portion 2, a universal cord 4 extended at the proximal end (near end) from the side portion of the operating portion 3, and a connector 5 mounted to the end (far end) of the universal cord 4. A light guiding cap 6 is projected from the end of the connector 5, and is attached to a light source device (not shown). Thus, illumination light is supplied from the light source device and the illumination light is transmitted by light guiding fibers inserted in the endoscope 1. The light is outputted from an illumination window at the end (distal end) of the inserting portion 2 and an examination target portion such as the affected part is illuminated.

An electric connector portion 7 is mounted on the side surface of the connector 5. The electric connector portion 7 is attached to a video processor via a connecting cable (not shown) attached thereto, and the video processor is thus electrically connected to an image pick-up device, which will be described later, included in the endoscope 1. The video processor applies a driving signal to the image pick-up device, performs the signal processing of an image pick-up signal picked up by the image pick-up device, and generates a video signal. The video processor further outputs the generated video signal to a monitor (not shown), and displays an image picked up by the image pick-up device on a display surface of the monitor.

A hard distal end portion 8, a bending portion 9 which is freely bent, and a flexible portion 10 with flexibility are sequentially mounted from the distal end side of the inserting portion 2, and the proximal end of the flexible portion 10 reaches the operating portion 3. The operating portion 3 has, on the front end side thereof, a grip portion 11 which is gripped by an operator. The grip portion 11 includes, at the front end thereof, a connecting member for connection to the inserting portion 2.

A bending lever 12 is mounted on the rear side (upper end or the top portion) of the grip portion 11 so as to operate the bending lever 12 by the hand gripping the grip portion 11. The bending lever 12 is operated, the bending portion 9 is bent, and the distal end portion 8 is thus vertically bent. The endoscope 1 according to the first embodiment has the structure of the bending portion 9 which can be bent only in the vertical direction so that the inserting portion 2 has the thin diameter.

A video switch portion 13 is mounted at the proximal end of the operating portion 3 for the remote operation of freeze and release, on the video processor side.

An inserting slit 14 of a treatment tool such as a clamp is mounted near the front end of the grip portion 11. The treatment tool inserted from the inserting slit 14 can be inserted in a channel mounted in the longitudinal direction of the inserting portion 2.

Light guiding fibers (not shown) and a signal cable connected to the image pick-up device are inserted into the universal cord 4 extended in the direction perpendicular to the side surface of the operating portion 3 therefrom.

Next, the configuration of the inserting portion 2 on the distal end side thereof will be described with reference to FIG. 2.

Referring to FIG. 2, the distal end portion 8 is formed by a distal end portion main body 16 which is made of a hard member such as metal with substantially cylindrical shape. A plurality of holes are provided in the axial direction of the distal end portion main body 16, and the holes are fixedly filled with various components.

For example, an objective lens system (objective optical system) 18 is fixed to the hole of an observing window via a lens frame 17 or the like. Distal end surfaces of image guiding fibers 19 having a function of transmitting means of an optical image (optical information) are fixed at the position for forming the image of the objective lens system 18. The image guiding fibers 19 transmit the optical image formed onto the distal end surface thereof to a proximal end surface (output end surface) mounted in the operating portion 3.

The distal end of a flexible tube 21 forming a channel 20 inserted in the inserting portion 2 is fixed to the proximal end of the hole provided adjacently to the observing window via a cap member 22. The proximal end side of the channel 20 is branched in the halfway, one branched channel 20 is connected to the inserting slit 14, and the other branched channel 20 is extended to the proximal end side of the operating portion 3. The distal end of the channel 20 is opened via the hole of the distal end portion main body 16.

Light guiding fibers (not shown) are inserted in the inserting portion 2 and the distal ends of the light guiding fibers are fixed to the hole for illuminating window of the distal end portion main body 16, and output illumination light from the fixed distal end surface. The light illuminates the subject within the observing range of the objective lens system 18.

A bending piece (node ring) 23 at the last end with substantially circular shape is fixed to the proximal end of the distal end portion main body 16, and the distal end of the bending piece 23 as the succeeding one is rotatably connected to the proximal end of the bending piece 23 via a rotating and connecting member using a rivet 24 or the like at the position in a predetermined direction such as the right or left direction. Thus, the many bending pieces 23 are rotatably connected in the longitudinal direction of the inserting portion 2 and the bending portion 9 is formed.

A pair of bending wires 25 is inserted along the position apart from the connecting position using the rivet 24, for example, the position in the vertical direction, and the distal end of the bending wire 25 is strongly fixed to the endmost bending piece 23 by waxing.

The proximal ends of the pair of bending wires 25 are fixed to a drum 32a forming a drum unit 32 as a bending mechanism of the operating portion 3 as shown in FIGS. 3A and 3B. The drum 32a is rotated by rotating the bending lever 12, pulls one of the pair of the bending wires 25, and releases the other of the pair of the bending wires 25. Thus, the bending portion 9 is bent to the bending wire 25 side on the pulled side.

Referring to FIG. 2, the bending portion 9 is covered with a net tube 28 and a bending rubber tube 29 made of elastic resin which covers the outside of the net tube 28.

Next, a description is given of the operating portion 3 and the grip portion 11 with reference to FIGS. 3A to 5. FIG. 3A mainly shows the internal configuration of the operating portion 3 on the proximal end side, FIG. 3B shows a diagram in a direction of an A arrow shown in FIG. 3A, FIG. 4A shows the internal configuration of the periphery of the grip portion on the front side of the operating portion, and FIGS. 4B to 4E show cross-sections by a C-C, E-E, F-F, and G-G lines shown in FIG. 4A, respectively.

Referring to FIGS. 3A and 3B, the proximal end side of the operating portion 3 is covered with exterior members 31a and 31b of the operating portion. The video switch portion 13 is attached at the proximal end of the operating portion 3. The drum unit 32 forming the bending mechanism is mounted to one side surface of the proximal end of the operating portion 3. The drum unit 32 is connected to the bending lever 12. A bending-preventing member 33 is mounted on the side surface facing the one side surface of the operating portion 3 having the drum unit 32, and the universal cord 4 is extended by the bending-preventing member 33.

A connecting portion 36 is formed on the front end sides of the exterior members 31a and 31b of the operating portion, and the exterior members 31a and 31b of the operating portion are connected to an exterior member 35 of the grip portion to be resolved. That is, in the connecting portion 36, the proximal end of the exterior member 35 of the grip portion which covers the grip portion 11 is fit into the exterior members 31a and 31b of the operating portion via a watertight O ring 37. The exterior member 31b of the operating portion is connected to the exterior member 31a of the operating portion via the watertight O ring 34 to be resolved each other.

Referring to FIG. 4A, a bending-preventing member 38 is mounted at the front end of the exterior member 36 of the grip portion and a flexible tube of the inserting portion 2 is connected to the bending-preventing member 38. The inserting slit 14 is mounted near the front end of the exterior member 35 of the grip portion so as to insert the treatment tool. The inserting slit 14 becomes the channel 20 which is in the conjunction of an absorbing tube 40 via a branching member 39. FIG. 4B shows the configuration of the periphery of the branching member 39.

The exterior member 35 of the grip portion accommodates the absorbing tube 40, the above-mentioned image guiding fibers 19, the light guiding fibers (not shown), and the coils 43 (refer to FIG. 3A) through which the wire 25 is inserted. The wire 25 is advanced and returned to perform the bending operation.

The components are protected by the exterior member 35 of the grip portion. Further, a plate frame 45 made of a hard member such as metal is mounted as an internal structure in the exterior member 35 of the grip portion. Thus, the deformation of the exterior member 35 of the grip portion is suppressed and the components are protected without fail.

The frame 45 is substantially rectangular-plate-shaped. Referring to FIG. 3A, the proximal end of the frame 45 is L-bent, and fixed to the exterior member 31a of the operating portion near the connecting portion 36 by a screw 46.

According to the first embodiment, referring to FIG. 3B, the frame 45 has a notch portion 45a which is formed by notching a part of the proximal end of the substantially rectangular-shaped frame 45 from the side direction. An electrical unit, specifically, an image pick-up unit 47 is mounted to a space formed by the notch portion 45a, thereby compactly accommodating the image pick-up unit 47 in the grip portion 11.

Referring to FIGS. 3B, 4A, and 5, the frame 45 is mounted in the longitudinal direction thereof near in the center of the grip portion 11. The frame 45 has the notch portion 45a which is formed by notching a part thereof on the proximal end side at the deviated position in the exterior member 35 of the grip portion. According to the first embodiment, the image pick-up unit 47 is mounted to the deviated position of the notch portion 45a.

The image pick-up unit 47 is mounted substantially in parallel with the longitudinal direction of the operating portion 3. Specifically, referring to FIG. 5, the image pick-up unit 47 is mounted in parallel with the exterior member 35 of the grip portion along the inner shape thereof.

As will be described later, the exterior member 35 of the grip portion has components such as the wire 25 for the bending operation. The image pick-up unit 47 is mounted substantially in parallel with the inner surface of the exterior member 35 of the grip portion adjacently thereto, thereby efficiently mounting the image pick-up unit 47 while preventing the components.

Referring to FIG. 5, the image pick-up unit 47 comprises: a hard fiber supporter 52 which holds a hard cap 51 for protecting the proximal ends of the image guiding fibers 19 with substantially cylindrical shape; a relay optical system 53 which is mounted facing a proximal end surface (output end surface) 19a of the image guiding fibers 19 and has a function for forming an image with a desired magnification; and an image pick-up portion 55 which is mounted at the position for forming the optical image transmitted to the proximal end surface 19a of the image guiding fibers 19 by the relay optical system 53 and which has a charge coupled device (hereinafter, abbreviated to a CCD) 54 as an image pick-up device having a function for photoelectrically converting the image. A signal cable 56 connected to the image pick-up portion 55 is extended on the rear side from the proximal end of the image pick-up portion 55.

The fiber supporter 52 for holding the cap portion 51 near the proximal end of the image guiding fibers 19 is fixed to a fixing frame 57 mounted to the outer periphery thereof at two positions in the longitudinal direction. Referring to FIG. 4D, one end portion side of the fiber supporter 52 is positioned, adjusted, and fixed by three screws 58 from three peripheral directions. Referring to FIG. 5, another end portion side of the fiber supporter 52 is fixed by screws 58' from three peripheral directions.

Referring to FIG. 4E, the fixing frame 57 is fixed to an outer frame 59 on the outer-peripheral side by a screw 60. The fixing frame 57 of the image pick-up unit 47 is fixed to an L-shaped attaching member 63 by a screw 62.

The relay optical system 53 facing the output end surface 19a (refer to FIG. 5) of the image guiding fibers 19 held by the fiber supporter 52 is attached to a lens frame 65. The front end side of the lens frame 65 is fit into the outer frame 59, and a CCD frame 54a of the CCD 54 is positioned, adjusted, fixed to the proximal end side of the lens frame 65. That is, the relay optical system 53 adjusts the CCD 54 so that the image pick-up surface of the CCD 54 is positioned at the position for forming the image with predetermined size.

A portion at which the lens frame 65 is fit into the outer frame 59 is fixed by adjusting the focusing of the relay optical system 53 in the optical axis direction by using a screw 66. The optical image transmitted to the output end surface 19a of the image guiding fibers 19 is adjusted so that it is formed onto the image pick-up surface of the CCD 54 via the relay optical system 53 clearly with predetermined size. Then, the image pick-up unit 47 is attached, by using the attaching member 63, near the notch portion 45a which is formed by notching the frame 45.

In this case, the fixing position of the fiber supporter 52 is adjusted, by using the screw 58, from three peripheral directions. As mentioned above, the central axis of the output end surface 19a of the image guiding fibers 19 matches the optical axis of the relay optical system 53 and then the image pick-up unit 47 is attached to the frame 45 by the attaching member 63.

Inserted into the grip portion 11 are components such as the image guiding fibers 19, the absorbing tube 40, and the coil 43 as a guiding member into which the wire 25 for bending operation is inserted. The coil 43 and the like are held by a coil supporter 67 (refer to FIG. 4C) fixed to the frame 45. Referring to FIG. 4C, the frame 45 has the end portion on the bottom in the drawing which is L-bent, with predetermined strength in the direction vertical to the plate surface.

According to the first embodiment, the image pick-up unit 47 is attached (fixed) to the frame 45 by the L-shaped attaching member 63. With the structure for attaching the image pick-up unit 47 to the frame 45 via the attaching member 63, the attaching member 63 is shaped to match the attachment of the image pick-up unit 47, and an attaching portion of the attaching member 63 and the plate frame 45 have a long hole. Therefore, the position of the image pick-up unit 47 is adjusted within a predetermined range and the image pick-up unit 47 is adjacent to the proper position, preferably, the inner peripheral surface of the exterior portion of the grip portion 11. The image pick-up unit 47 is simply fixed at the position where space in the grip portion 11 can be wide.

The image pick-up unit 47 is mounted at the position deviated from the center portion of the grip portion 11. As compared with the mounting of the image pick-up unit 47 near the center, the image pick-up unit 47 is easily subjected to the optical adjustment.

Referring to FIG. 5, a flange portion 69 is mounted at the front end portion of the image pick-up unit 47, adjacently to the screw 58, in other words, at the front end portion of the fixing frame 57 in the example. The flange portion 69 regulates the movement of the distal end of a driver at an erroneous position which is caused by the slide of the driver distal end or the like upon adjusting the screw 59 with the driver, and the contact state of the driver distal end with the image guiding fibers 19 is prevented.

Referring to FIG. 3B, the front end side of the notch portion 45a may diagonally be notched as shown by a dotted line L from a shape shown by a solid line so as to provide the notch portion 45a for the frame 45. Thus, the sandwiching of the image guiding fibers 19 by the front end portion of the notch portion 45a is solved upon fixing the image pick-up unit 47 to the notch portion 45a.

According to the first embodiment, the image pick-up unit 47 has the CCD 54 which picks up the optical image transmitted by the image guiding fibers 19 and which photoelectrically converts the optical image. The image pick-up unit 47 is mounted to the notch portion 45a which is formed to the frame 45 as the internal structure in the grip portion 11 on the front end side of the operating portion 3, and is fixed to the frame 45 by the attaching member 63. As a consequence, the image pick-up unit 47 is fixed to the frame 45 by the attaching member 63 and, therefore, the endoscope 1 for compactly accommodating the image pick-up unit 47 is realized with the simple structure while the predetermined strength is ensured.

The image pick-up unit 47 is mounted at the position of the notch portion 45a deviated from the center of the grip portion 11, and the optical adjustment or maintenance of the image pick-up unit 47 is easy.

That is, as compared with the case of mounting the image pick-up unit 47 near the center of the grip portion 11, the center of the output end surface 19a of the image guiding fibers 19 is deviated from the optical axis of the relay optical system 53 as a result of the use of the image pick-up unit 47 for a long time and, then, the optical axis is easily corrected by the position adjusting using the screw 58 or the like.

Specifically, referring to FIG. 4E, the image pick-up unit 47 is deviated and attached and therefore the image pick-up unit 47 is re-adjusted by using the screw 58 from three directions while the image pick-up unit 47 is attached to the frame 45 via the attaching member 63.

According to the first embodiment, advantageously, the image pick-up unit 47 includes the CCD 54 which picks up the optical image transmitted by the image guiding fibers 19 and which photoelectrically converts the image, and it is compactly accommodated in the grip portion 11 on the front end side of the operating portion 3 with the simple structure while assuring the predetermined strength.

That is, according to the first embodiment, advantageously, the endoscope includes, on the front end side of the operating portion, the function for inserting and absorbing the wire for bending operation and the treatment tool, and the endoscope apparatus has not only the endoscope and other components but also the internal structure such as the plate frame in the operating portion so as to fix the components and to ensure the necessary strength.

According to the first embodiment, the image pick-up unit is accommodated on the front end side of the operating portion. Thus, as compared with the case in which the image pick-up unit is provided in the operating portion near the proximal end thereof, the loss of the light amount caused by the optical fiber is reduced and the image with a higher S/N ratio is obtained.

The image pick-up unit 47 according to the first embodiment has the structure having a waterproof structure portion.

(a) For example, referring to FIG. 5, the position of the lens frame 65 is adjusted so that the optical image transmitted by the relay optical system 53 is formed onto the image pick-up surface of the CCD 54. Then, the CCD frame 54a and the lens frame 65 are watertightly fixed with an adhering agent.

(b) Referring to FIG. 3B, the image pick-up unit 47 has a simple waterproof structure which is obtained by winding a waterproof film sheet 70 shown by a two-dotted line to the image pick-up unit 47. The waterproof film sheet 70 is not wound to the periphery portion of the attaching member 63 and therefore a sealing member such as an O ring may partly be used.

As mentioned above, the following advantages are obtained with the structure having the waterproof structure portion.

That is, since the lens frame 65 is adhered to the CCD frame 54a, the flow of a solution such as water from the fitting portion toward the CCD 54 is prevented. Further, since the entire image pick-up unit 47 has a simple waterproof structure, the image pick-up unit 47 does not easily come into contact with the solution such as water.

The inspection of periphery devices after/before the endoscope examination generally detects a trouble of the exterior member 35 or damage of the waterproof structure of the grip portion 11. That is, as shown by the structures (a) and (b), the structure for preventing the easy flow of the solution into the CCD 54 prevents the trouble of the expensive CCD 54 upon the damage of the waterproof structure of the endoscope 1.

According to the first embodiment, the image pick-up unit 47 is described as an example but, alternatively, an electric device other than the image pick-up unit may be mounted.

Second Embodiment

Next, the second embodiment of the present invention will be described with reference to the drawings.

Figure 6:
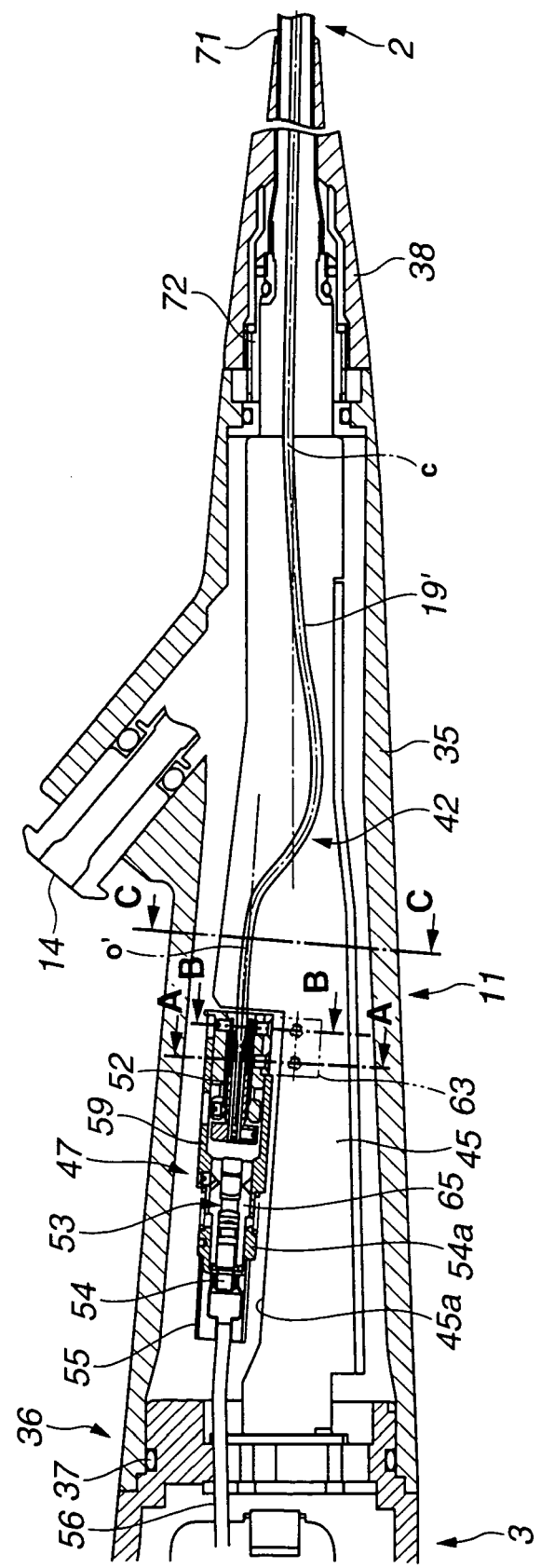
FIG. 6 is a cross-sectional view showing the internal configuration of the periphery of a grip portion in an operating portion according to a second embodiment of the present invention.
Figure 7:
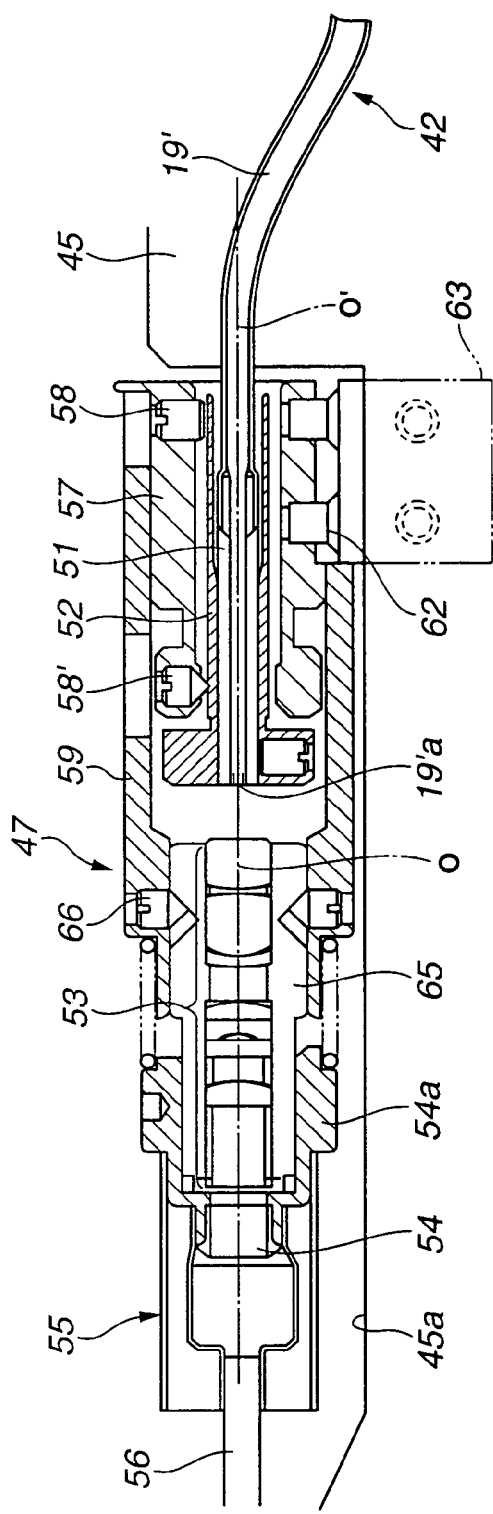
FIG. 7 is an enlarged cross-sectional view showing an image pick-up unit shown in FIG. 6.

FIGS. 6 and 7 relate to the second embodiment of the present invention, FIG. 6 is a diagram showing the internal structure of an operating portion, and FIG. 7 is an enlarged view showing an image pick-up unit shown in FIG. 6. According to the second embodiment, only image guiding fibers 19' are used, unlike the first embodiment, and the appearance of the endoscope according to the second embodiment and the internal structure of the inserting portion on the distal end side are those shown in FIG. 1 or 2. The enlarged cross-sectional views of the A-A, B-B, and C-C cross sections shown in FIG. 6 are the same as those shown in FIGS. 4E, 4D, and 4C.

A description is given of the internal structure of the operating portion 3, specifically, the internal structure of the grip portion 11 which is gripped by an operator on the front end side of the operating portion 3 with reference to FIGS. 6 and 7.

An exterior member of the operating portion 3 comprises the exterior member 35 of the grip portion which covers the grip portion 11 on the front end side of the operating portion 3, and exterior members 31a and 31b of the operating portion which cover the operating portion main body on the proximal end side. The exterior members 35 of the grip portion and the exterior members 31a and 31b of the operating portion are connected at a connecting portion 36 for fitting them each other via a watertight sealing member such as the O ring 37.

As mentioned above, the substantially-plate frame 45 is mounted in the exterior member 35 of the grip portion (hereinafter, abbreviated to the exterior member 35) as the internal structure for ensuring predetermined strength. One end (proximal end) of the frame 45 in the longitudinal direction is bent like L and is fixed by a screw (not shown) to the exterior members 31a and 31b of the operating portion in the connecting portion 36, and another end reaches near the front end of the grip portion 11.

A branch member 39 is branched to the inserting slit 14 side and the absorbing tube 40 side. The absorbing tube 40 extended to the operating portion 3 side is indicated as the cross section in FIG. 4C. The branch portion 39 is fixed near the front end of the frame 45.

An exterior member of the inserting portion 2 is formed at a flexible tube 71. The image guiding fibers 19' are inserted into a hollow portion of the flexible tube 71. The proximal end of the flexible tube 71 is connected to the exterior member 35 near the front end of the grip portion 11 via a connecting member 72.

It is possible to prevent the sharp bending of the boundary of the grip portion 11 at the proximal end of the flexible tube 71 by using the bending preventing member 38 which is taper-shaped with the larger thickness on the rear side.

The image guiding fibers 19' with the flexibility inserted in the inserting portion 2 are inserted along the substantially the central axis of the flexible tube 71, and are substantially straight extended on the rear side as shown by the central line as a one-dotted line C by the bending preventing member 38 which is taper-shaped near the proximal end of the inserting portion 2 (in the state in which the large bending is suppressed).

According to the second embodiment, the image guiding fibers 19' are substantially straight extended toward the grip portion 11 side on the back as shown by the one-dotted line C in the bending preventing member 38 which is taper-shaped near the proximal end of the inserting portion 2. The output end portions of the image guiding fibers 19' at the proximal ends thereof are fixed while a bending portion (play portion) 42 is formed to the image pick-up unit 47 attached to the grip potion 11 deviated from the substantially straight line shown by the one-dotted line C.

That is, referring to FIG. 6, the notch portion 45a is mounted in the grip portion 11. The notch portion 45a is notched from the side perpendicular to the longitudinal direction of the substantially-rectangular frame 45 on the proximal end side, extended elongated in the longitudinal direction. The cylindrical image pick-up unit 47 is mounted to the notch portion 45a. Referring to FIGS. 4E and 4D, the image pick-up unit 47 is fixed to the frame 45 via the L-shaped attaching member 63 attached to the frame 45 using the screw 64.

According to the second embodiment, the frame 45 mounted substantially in the center of the grip portion 11 is partly notched from the side (on the upper side shown in FIG. 6), and the image pick-up unit 47 is mounted and fixed to the notch portion 45a formed at the position deviated from the center of the grip portion 11 in the longitudinal direction.

Referring to FIG. 7, the image pick-up unit 47 is enlarged. The image pick-up unit 47 comprises the substantially cylindrical hard fiber supporter 52 which holds the hard cap portion 51 such as metal for protecting the output end portion at the proximal end of the image guiding fibers 19, the relay optical system 53 which is mounted facing output end surfaces 19'a of the image guiding fibers 19' and which includes a function for forming the optical image transmitted to the output end surface 19'a with a desired magnification, and an image pick-up portion 55 which is mounted at the position for forming the image with predetermined size by the relay optical system 53 and which has a charge coupled device (abbreviated to a CCD) 54 as the image pick-up device having a photoelectrically converting function. The signal cable 56 is extended to the back side from the proximal end of the image pick-up unit 55.

According to the second embodiment, the relay optical system 53 for forming the image with desired size is used. For the purpose of low costs, an image forming optical system may be used with a function for forming an optical image transmitted to the proximal end surface 19'a of the image guiding fibers 19' with predetermined size.

The fiber supporter 52 holds the cap 51 portion near the proximal end of the image guiding fibers 19', and is fixed to the fixing frame 57 mounted to the outer periphery at two positions in the longitudinal direction. For example, referring to FIG. 4D, one end portion of the fiber supporter 52 is adjusted for its position and is fixed at the three screws 58 in three peripheral directions. Referring to FIG. 7, positions near another end of the fiber supporter 52 are fixed at screws 58' at three positions in the peripheral direction.

Referring to FIG. 4E, the fixing frame 57 is fixed to the outer frame 59 on the outer peripheral side by the screw 60. The fixing frame 57 of the image pick-up unit 47 is fixed to the L-shaped attaching member 63 by the screw 62.

The relay optical system 53 faces the output end surfaces 19'a (refer to FIG. 7) of the image guiding fibers 19' held by the fiber supporter 52, and is attached to the lens frame 65. The front end side of the lens frame 65 is fit into the outer frame 59, and the CCD frame 54a of the CCD 54 is adjusted and is fixed on the proximal end side of the lens frame 65. That is, the. CCD frame 54a is fixed to the lens frame 65 while the relay optical system 53 adjusts the CCD frame 54a so that the image pick-up surface of the CCD 54 is at the position for forming the optical image of the relay optical system 53 with predetermined size.

A portion at which the lens frame 65 is fit into the outer frame 59 is fixed by adjusting the focusing of the relay optical system 53 in the optical axis direction by using the screw 66. The optical image transmitted to the output end surfaces 19'a of the image guiding fibers 19 is adjusted so that it is formed onto the image pick-up surface of the CCD 54 via the relay optical system 53 clearly with predetermined size. Then, the image pick-up unit 47 is attached, by using the attaching member 63, near the notch portion 45a which is formed by notching the frame 45.

In this case, the fixing position of the fiber supporter 52 is adjusted, by using the screw 58, from three directions in the peripheral directions. On the output end surfaces 19'a of the image guiding fibers 19', a central axis O' of the output end surfaces 19'a matches an optical axis O of the relay optical system 53.

Referring to FIG. 4C as the C-C cross section of FIG. 6, inserted into the grip portion 11 are the image guiding fibers 19, and components such as the absorbing tube 40 and the coil as a guiding member into which the wire for bending operation is inserted. The coil and the like are held by the coil supporter 67 fixed to the frame 45 at the position shown in FIG. 4C. Referring to FIGS. 4E to 4C, the frame 45 has the end portion on the bottom in the drawing which is L-bent, with predetermined strength in the direction vertical to the plate surface.

According to the second embodiment, the output end portions of the image guiding fibers 19' inserted in the inserting portion 2 are fixed to the fiber supporter 52 of the image pick-up unit 47 partly fixed to the deviated position from the center position in the grip portion 11, not so that the image guiding fibers 19' are straightly extended, but so that the bending portion 42 which is smoothly bent from the straight state (and a space portion for freely modifying the bending portion 42) is formed.

That is, referring to FIG. 6, the image guiding fibers 19' are extended along substantially the center line C on the back from the proximal end portion of the inserting portion 2, and are fixed to the image pick-up unit 47 via the portion bent by the bending portion 42 in the grip portion 11 so that the proximal end portions of the image guiding fibers 19' are on the central axis O'.

As mentioned above, the image pick-up unit 47 is adjusted and then is attached in the grip portion 11. After attaching the image pick-up unit 47, it is finely adjusted.

Thus, according to the second embodiment, referring to FIGS. 6 and 4D, the screws 58 in the three directions are easily adjusted by a driver (not shown) via the opening mounted to the outer frame 59.

In this case, referring to FIG. 6, the image pick-up unit 47 is mounted at the position deviated from the center of the grip portion 11 by the notch portion 45a. As compared with the case in which the image pick-up unit 47 is mounted substantially in the center, the working for fine adjustment becomes easy without the obstacle of the components. The screw 66 for fixing the lens frame 65 and the outer frame 59 can easily be fixed by the re-adjustment.

According to the second embodiment, the front and proximal ends of the image guiding fibers 19' are fixed, therebetween, specifically, in the grip portion 11, the bending portion 42 is formed. The inserting portion 2 is curved or bent and tension acts at the front and proximal ends of the image guiding fibers 19', then, the image guiding fibers 19' are modified at the position of the bending portion 42, the tension is absorbed, and it does not act to the image guiding fibers 19'. In the image pick-up unit 47, a predetermined image pick-up function is maintained.

For example, the bending operation is repeated and the tension is to act to the front and proximal ends of the image guiding fibers 19' in accordance with the bending operation and, then, the modification of the image guiding fibers 19' at the position of the bending portion 42 solves the influence from the tension or reduces it. The predetermined image pick-up function is maintained for a long time period with the simple structure.

If the lengths in the image guiding fibers 19' vary in the manufacturing, the change in the bending amount in the bending portion 42 fixes the image guiding fibers 19' without changing the fixing position in the grip portion 11. That is, the allowable varying amount is increased for the lengths of the image guiding fibers 19' and the manufacturing costs are reduced.

Further, the deviation of the central axis enables the image pick-up unit 47 fixedly having the image guiding fibers 19' to be attached to the frame 45 while easily avoiding other components such as the coil serving as the guiding member into which the absorbing tube 40 or the wire 25 is inserted. Upon assembly, the danger to bend the image guiding fibers is reduced.

Third Embodiment

Next, the third embodiment of the present invention will be described with reference to FIG. 8.

As mentioned above according to the second embodiment, the formation for the bending portion 42 solves or suppresses the influence from the bending of the inserting portion 2 or from the variation in lengths of the image guiding fibers 19'. Further, the image pick-up unit 47 may be fixed to the frame 45 by adjusting the bending amount of the image guiding fibers 19', which will be described hereinbelow.

Figure 8:
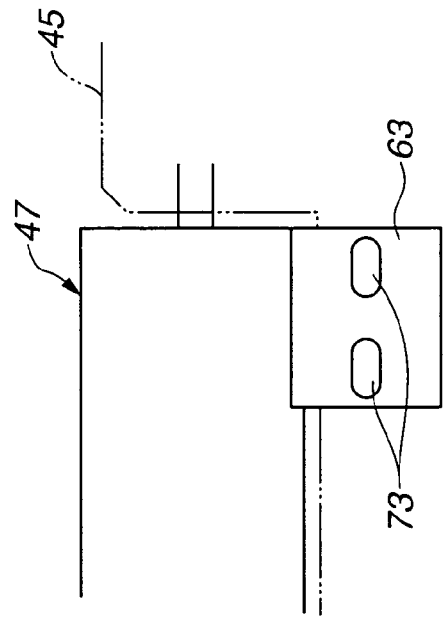
FIG. 8 is a side view showing an attaching member for attaching an image pick-up unit according to a third embodiment of the present invention.

FIG. 8 shows a view of the attaching member 63 in the bottom direction on the sheet in FIG. 7 (a state inverse to the right and left for the purpose of the same direction of the right and left in FIG. 7). Referring to FIG. 8, the attaching member 63 has a long hole 73 which is long in the longitudinal direction (right and left direction in FIG. 8) of the grip portion 11. The long hole 73 adjusts the position for fixing the image pick-up unit 47 to the frame 45 by the screw 64 via the attaching member 63 (in the longitudinal direction of the grip portion 11).

The attaching member 63 may be fixed to the frame 45 at the position near the proximal end of the grip portion 11, that is, at the position near the left in FIG. 8 so as to decrease the bending amount. On the contrary, the attaching member 63 may be fixed to the frame 45 at the position near the front end of the grip portion 11, that is, at the position near the right in FIG. 8 so as to increase the bending amount. A screw hole is formed to which the screw 64 is screwed on the frame 45 side.

If the lengths of the image guiding fibers 19' vary, the same bending amount is set for the products depending on the fixing position of the attaching member 63 to fix the image pick-up unit 47.

According to the third embodiment, in addition to the advantages according to the second embodiment, the variation in lengths of the image guiding fibers 19' is absorbed and the bending amount is properly adjusted. Advantageously, the endoscope is provided without bending the image guiding fibers and reducing manufacturing costs thereof.

Having described the predefined embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
an elongated flexible inserting portion;
an operating portion which is mounted on the proximal end side of the inserting portion and which has a grip portion capable of being gripped by an operator;
an objective optical system which is mounted to the distal end side of the inserting portion and which can transmit an optical image of a subject into the inserting portion;
image guiding fibers which can transmit the optical image incident from the distal end side via the objective system to the proximal end side and which is inserted into the inserting portion so that the proximal end side extends in the operation portion from the inserting portion;
an optical image output portion which constitutes the proximal end side of the image guiding fibers and which outputs the optical image transmitted from the distal end side;
an image pick-up unit having an image pick-up device for picking up the optical image transmitted from the optical image output portion; and
a plate frame provided in the operating portion for suppressing a deforming of the operating portion, the plate frame having a notch portion to mount the image pick-up unit at a position at which the optical image transmitted by the optical output portion can be picked up in the operating portion.

2. An endoscope according to claim 1, wherein the image pick-up unit is mounted substantially in parallel with the shape of the operating portion in the longitudinal direction thereof.

3. An endoscope according to claim 1, wherein the image pick-up unit is fixed to the plate frame via a mounting member.

4. An endoscope according to claim 1, further comprising:
an image pick-up unit holding portion which holds the image pick-up unit;
an optical system holding portion which holds the objective optical system;
a fitting portion which fits the optical system holding portion and the image pick-up unit holding portion while advancing and returning them so that the image pick-up unit can pick up the optical image outputted from the objective optical system; and
a waterproof structure portion mounted to the fitting portion.

5. An endoscope comprising:
an elongated flexible inserting portion; and
an operating portion which is mounted on the proximal end side of the inserting portion and which has a grip portion capable of being gripped by an operator, the endoscope further comprising:
an electric device outputting predetermined signals;
an internal structure mounted in the operating portion, which is inserted in the grip portion from the proximal end side thereof to the distal end side;
a notch portion mounted to the internal structure; electric device mounting means which is mounted to the internal structure and mounts the electric device within the notch portion,
a plate frame provided in the internal structure of the operating portion for suppressing a deforming of the operating portion, the plate frame having the notch portion to mount the electronic device.

6. An endoscope comprising:
an elongated flexible inserting portion;
a grip portion which is mounted on the proximal end side of the inserting portion and which can be gripped by an operator;
an objective optical system which is mounted to the distal end side of the inserting portion and which can transmit an optical image of a subject into the inserting portion;
image guiding fibers which can transmit the optical image incident from the distal end side via the objective optical system to the proximal end side and which is inserted to the inserting portion so that the proximal end side extends in the grip portion from the inserting portion;
an optical image output portion which constitutes the proximal end side of the image guiding fibers and which outputs the optical image transmitted from the distal end side;
an image pick-up unit which is provided in the grip portion and is optically connected to the optical image output portion and which has an image pick-up device capable of picking up the optical image transmitted from the optical image output portion,
a plate frame provided in the grip portion for surpressing a deforming of the grip portion, the plate frame having a notch portion to mount the image pick-up unit;
wherein the optical axis of the optical image outputted to the image pick-up unit from the optical image output portion is deviated from the central axis of a portion at which the image guiding fibers are extended in the grip portion.

7. An endoscope according to claim 6, further comprising:
adjusting and fixing means which can adjust the bending amount of the image guiding fibers and which fixes the image pick-up unit.

8. An endoscope according to claim 1, further comprising:
an attaching member for fixing the image pick-up unit to the plate frame; and
a screw for adjusting the position of the image pick-up unit, the screw being adjustable from a circumferential direction different from the direction of the attaching member with respect to the image pick-up unit.

9. An endoscope according to claim 6, further comprising:
an attaching member for fixing the image pick-up unit to the plate frame; and
a screw for adjusting the position of the image pick-up unit, the screw being adjustable from a circumferential direction different from the direction of the attaching member with respect to the image pick-up unit.

* * * * *